(12) United States Patent
Oeelund

(10) Patent No.: US 11,497,645 B2
(45) Date of Patent: Nov. 15, 2022

(54) OSTOMY APPLIANCE WASTE COLLECTION BAG WITH A MOLDED FRONT WALL THAT CONTINUOUSLY EXTENDS TO FORM BOTH A SIDE WALL AND A REAR WALL

(71) Applicant: Coloplast A/S, Humlebaek (DK)

(72) Inventor: Jakob Oeelund, Alleroed (DK)

(73) Assignee: Coloplast A/S, Humlebaek (DK)

( * ) Notice: Subject to any disclaimer, the term of this patent is extended or adjusted under 35 U.S.C. 154(b) by 988 days.

(21) Appl. No.: 16/134,970

(22) Filed: Sep. 19, 2018

(65) Prior Publication Data

US 2019/0015242 A1 Jan. 17, 2019

Related U.S. Application Data

(63) Continuation of application No. 14/437,504, filed as application No. PCT/DK2013/050339 on Oct. 22, 2013, now Pat. No. 10,105,254.

(30) Foreign Application Priority Data

Oct. 23, 2012 (DK) .............................. PA 2012 70644
Oct. 26, 2012 (DK) .............................. PA 2012 70658
Aug. 28, 2013 (DK) .............................. PA 2012 00483

(51) Int. Cl.
*A61F 5/44* (2006.01)
*A61F 5/443* (2006.01)
(Continued)

(52) U.S. Cl.
CPC .............. *A61F 5/4404* (2013.01); *A61F 5/44* (2013.01); *A61F 5/443* (2013.01);
(Continued)

(58) Field of Classification Search
CPC .......... A61F 5/44; A61F 5/4404; A61F 5/443; B29C 49/20; B29C 49/24; B29C 45/055;
(Continued)

(56) References Cited

U.S. PATENT DOCUMENTS 2,003,092 A    5/1935    Richards
3,646,936 A * 3/1972    Marsan .................. A61F 5/445
                                                               604/344
(Continued)

FOREIGN PATENT DOCUMENTS

GB        23887      10/1910
GB        19317      2/1911

*Primary Examiner* — Guy K Townsend
(74) *Attorney, Agent, or Firm* — Coloplast Corp., Coloplast A/S; Nick Baumann

(57) ABSTRACT

An ostomy appliance includes a waste collection bag that is molded to form a front wall that continuously extends to form both a side wall and a rear wall. The rear wall is spaced apart from the front wall when the waste collection bag is empty. A bottom of the waste collection bag is defined by a curved bottom wall that continuously extends from both the front wall and a rear wall. The waste collection bag is formed to include a longitudinal curvature within at least one of the front wall and the rear wall, and a connector is integrally molded into the rear wall of the waste collection bag around a waste inlet.

13 Claims, 9 Drawing Sheets

(51) Int. Cl.
    *B29C 45/00*        (2006.01)
    *B29C 49/24*        (2006.01)
    *B29C 49/20*        (2006.01)
    *B29C 49/06*        (2006.01)
    *B29C 45/16*        (2006.01)
    *B29L 31/00*        (2006.01)

(52) U.S. Cl.
    CPC .......... B29C 45/0055 (2013.01); B29C 49/20 (2013.01); B29C 49/24 (2013.01); *B29C 45/1684* (2013.01); *B29C 49/06* (2013.01); *B29C 2049/2017* (2013.01); *B29L 2031/7148* (2013.01)

(58) Field of Classification Search
    CPC ............... B29C 45/1684; B29C 49/06; B29C 2049/2017; B29L 2031/7148
    See application file for complete search history.

(56) References Cited

U.S. PATENT DOCUMENTS

| | | | | |
|---|---|---|---|---|
| 4,419,174 | A * | 12/1983 | Jensen | B29C 66/472 156/289 |
| 5,158,810 | A * | 10/1992 | Oishi | C08J 5/18 428/36.1 |
| 5,501,677 | A * | 3/1996 | Jensen | A61F 5/448 604/338 |
| 5,693,036 | A * | 12/1997 | Kilgour | B29C 45/4407 604/338 |
| 5,733,628 | A * | 3/1998 | Pelkie | A61F 13/513 442/293 |
| 5,889,140 | A * | 3/1999 | Watanabe | C08G 63/912 528/80 |
| 5,935,363 | A * | 8/1999 | Gilman | A61F 13/0276 156/289 |
| 6,093,276 | A * | 7/2000 | Leise, Jr. | A61F 5/448 604/338 |
| 6,106,507 | A * | 8/2000 | Botten | A61F 5/448 604/338 |
| 6,329,465 | B1 * | 12/2001 | Takahashi | H01B 3/441 525/240 |
| 6,764,473 | B2 * | 7/2004 | Morton | A61F 5/445 604/338 |
| 6,946,182 | B1 * | 9/2005 | Allgeuer | B29C 59/04 428/172 |
| 7,344,521 | B2 * | 3/2008 | Andersen | A61F 5/445 604/327 |
| 8,845,606 | B2 * | 9/2014 | Nguyen-Demary | A61F 5/448 604/338 |
| 9,931,239 | B2 * | 4/2018 | Chang | A61F 5/443 |
| 9,974,682 | B2 * | 5/2018 | Schertiger | A61F 5/4408 |
| 2002/0065363 | A1 * | 5/2002 | Wang | C08L 67/04 525/58 |
| 2003/0100870 | A1 * | 5/2003 | Villefrance | A61F 5/441 604/333 |
| 2003/0109838 | A1 * | 6/2003 | Morton | A61F 5/445 604/334 |
| 2005/0240163 | A1 * | 10/2005 | Andersen | A61F 5/441 604/335 |
| 2005/0258574 | A1 * | 11/2005 | Blum | A61F 5/445 264/454 |
| 2006/0083710 | A1 * | 4/2006 | Joerger | C08F 259/00 442/128 |
| 2007/0027434 | A1 * | 2/2007 | Pedersen | A61F 5/441 604/338 |
| 2007/0276346 | A1 * | 11/2007 | Poulsen | A61F 5/441 604/333 |
| 2008/0176023 | A1 * | 7/2008 | Bager | B29C 66/73921 156/272.8 |
| 2008/0268193 | A1 * | 10/2008 | Cherry | B32B 27/08 428/36.6 |
| 2008/0306459 | A1 * | 12/2008 | Albrectsen | A61F 5/441 604/333 |
| 2009/0171306 | A1 * | 7/2009 | Worsoee | A61F 5/441 29/428 |
| 2009/0227973 | A1 * | 9/2009 | Worsoee | A61F 5/441 264/299 |
| 2010/0010460 | A1 * | 1/2010 | Butler | A61F 5/441 604/333 |
| 2011/0092663 | A1 * | 4/2011 | Weinhold | C08J 3/12 528/308.1 |
| 2012/0179124 | A1 * | 7/2012 | Nguyen-Demary | A61F 5/448 604/335 |
| 2014/0163496 | A1 * | 6/2014 | Grum-Schwensen | A61J 1/00 604/338 |
| 2014/0364823 | A1 * | 12/2014 | Nguyen-Demary | A61F 5/445 604/335 |
| 2015/0265454 | A1 * | 9/2015 | Oeelund | B29C 45/0055 264/537 |

* cited by examiner

OSTOMY APPLIANCE WASTE COLLECTION BAG WITH A MOLDED FRONT WALL THAT CONTINUOUSLY EXTENDS TO FORM BOTH A SIDE WALL AND A REAR WALL

The invention relates to a collecting bag for use in an ostomy appliance (or an ostomy bag) that is blow-moulded—thus given a three-dimensional structure. Furthermore, the invention relates to methods of producing such a collecting bag.

BACKGROUND

In connection with surgery for a number of diseases in the gastro-intestinal tract, one of the consequences in many cases is that the patient is left with an abdominal stoma, such as a colostomy or an ileostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a two-piece appliance comprising a wafer and a collecting bag which may be coupled to and un-coupled from each other through a coupling. This means that the wafer does not need to be separated from the skin of the user as often as exchange of the collecting bag requires. The wafer only needs to be changed every third or fourth day depending on the user, whereas the collecting bag may be changed more than once per day.

An ostomy collecting bag typically comprises two layers of film material that is welded or glued along the edges of the bag.

SUMMARY OF THE INVENTION

The invention relates to a collecting bag for use in an ostomy appliance that has a rounded shape so that the transition from the side facing the user to the side facing away from the user follows a rounded curve, when seen in cross-section. The collecting bag may in another or related aspect be obtainable by extrusion or by injection blow-moulding. In the extrusion blow-moulding process, an endless tube is initially extruded and subsequently the tube is blow-moulded to provide the finished collecting bag. In the injection blow-moulding process, a pre-form is initially injection moulded and subsequently the pre-form is blow-moulded to provide the finished collecting bag. Attachment means may be insert moulded in the blow-moulding process. A collecting bag according to the invention may be truly three-dimensional. Furthermore, the collecting bag has no sealed edges that provide reduced flexibility of the collecting bag along the edges.

BRIEF DESCRIPTION OF THE DRAWING

FIGS. 2 and 3 illustrate cross-sectional views of two embodiments of the collecting bag and FIG. 4 illustrates a perspective view of the collecting bag.

FIG. 15A illustrates a cross-section of the mould and the bag, and FIG. 15B illustrates a front view of the finished bag.

DETAILED DESCRIPTION OF THE INVENTION

Figure 1:
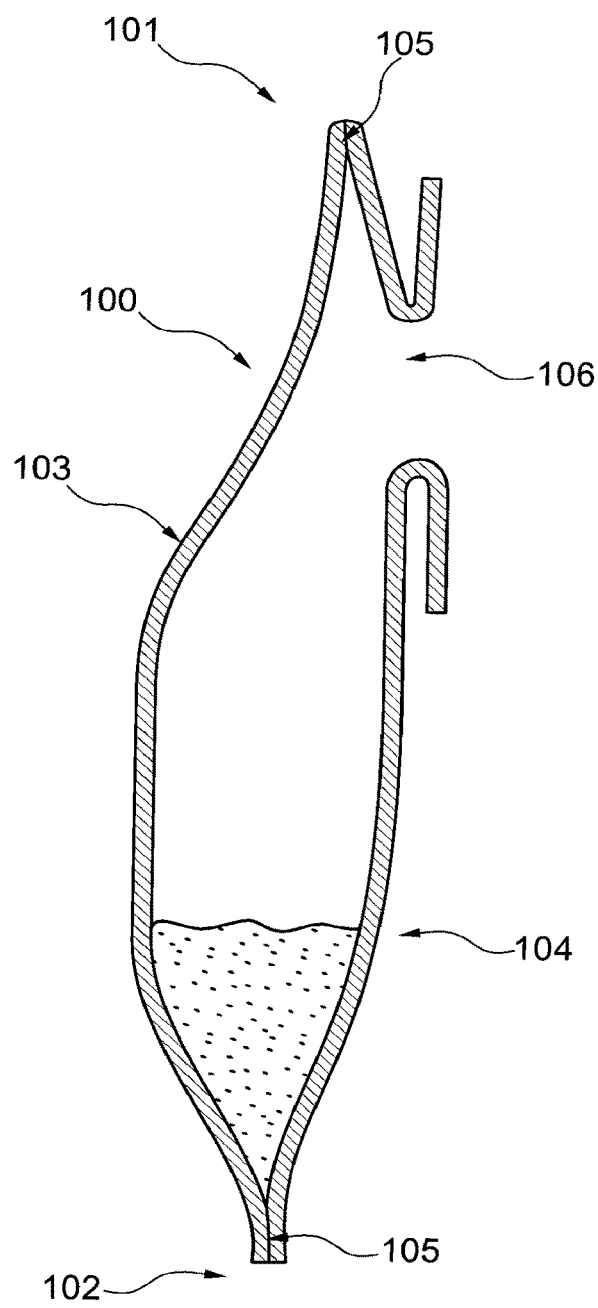
FIG. 1 illustrates a prior art ostomy bag.

In a first aspect, the invention relates to a collecting bag for use in an ostomy appliance, where the collecting bag comprises a generally continuous foil material defining a continuous wall of the collecting bag, with a front of the wall facing away from the user and a rear of the wall facing the user, where the transition between the front of the wall and the rear of the wall is smooth and defines a rounded curvature.

By generally continuous foil is meant that the collecting bag is provided in one piece of foil material so that the collecting bag has no sealed edges. By a smooth transition is meant that there are no sharp edges in the transition between the front of the wall and the rear of the wall—rather the transition from the front to the rear of the wall is not well-defined and the transition is a rounded curvature. This means that the cross-section defines a smooth curve in a sectional view of the collecting bag.

In a second aspect, the invention relates to a collecting bag for use in an ostomy appliance wherein the collecting bag is obtained by injection blow-moulding.

In a third aspect, the invention relates to a collecting bag for use in an ostomy appliance that is obtained by extrusion blow-moulding.

Ostomy bags (or collecting bags for use in ostomy appliances) are typically made by joining two or more films into a collecting bag, thus these prior art bags typically have well-defined front and rear walls. The joining in these prior art bags are typically made by either welding or gluing. A collecting bag according to the first, second and/or third aspect of the invention has no joined edges and is therefore more flexible than a prior art bag. Furthermore, such a collecting bag is able to benefit from the full volume of the collecting bag since the output can be stored at all positions inside the bag and is not limited by joined edges that may provide un-fillable volumes of the collecting bag. For thick output, the un-fillable volume of a collecting bag may be as large as 5% or 10% of the volume of the bag. Finally, there is no risk of leaking through joined edges in collecting bag according to the first, second or third aspect of the invention.

In other words, an ostomy collecting bag with joined edges has to have a larger surface area to provide the same interior collecting volume as an ostomy collecting bag having no joined edges. It is an advantage for the user to provide an ostomy collecting bag having as small a surface as possible, so as to make the collecting bag as inconspicuous as possible.

The sealed edges alone provide an increase in the surface of up to 5 mm around the entire periphery of the bag. For a generally oval bag that is about 200 mm long and about 100 mm wide the increase in surface area caused by the sealed edges may amount to between 10% and 15%.

Moreover a collecting bag having no sealed edges (without a well-defined front wall and rear wall) will be less likely to be subject to pancaking—that is, the situation where the front wall and the rear wall of the ostomy bag cling to each other. Pancaking is a well-know problem for ostomy appliances and may in extreme situations lead to problems of storing the output in the collecting bag. A collecting bag according to the first, second or third aspect, will naturally assume a position in which the front of the wall and the rear of the wall have a distance between them. This distance will minimise the risk of pancaking.

The collecting bag according to the first aspect may be obtained by either injection blow-moulding or extrusion blow-moulding. This means that the first aspect may be combined with the second aspect or the third aspect of the invention.

In a fourth aspect, the invention relates to a method of producing a collecting bag for use in an ostomy appliance comprising the steps of
  a) Injection moulding a pre-form
  b) Inserting the pre-form into a blow-moulding machine
  c) Blow-moulding the collecting bag In a fifth aspect, the invention relates to a method of producing a collecting bag for use in an ostomy appliance comprising the steps of
  a) Extruding a tube
  b) Inserting the tube into a blow-moulding machine
  c) Blow-moulding the collecting bag Collecting bags for ostomy appliances are typically made by joining two or more films into a collecting bag. When the collecting has been welded or glued the remaining part sticking out from the edges are cut-off—which leads to waste.

Injection moulding a pre-form and subsequently blow-moulding the collecting bag is an easy process to control because a standard pre-form can be used for a variety of bags and then the finish of the bag can be controlled by the mould used in the blow-moulding process.

Extrusion blow-moulding is a fast and easy process that can run continuously.

The process of extrusion blow-moulding is well-known and includes melting and extruding the material into a hollow tube (sometimes called a parison) and then subsequently inserting the hollow tube into a cavity of a mould. The melting may be provided by heating the material to e.g. approximately 140° C. or 160° C. depending on the material.

In the following, whenever referring to proximal side of a device or part of a device, the referral is to the skin-facing side, when the ostomy collecting bag is worn by a user. Likewise, whenever referring to the distal side of a device or part of a device, the referral is to the side facing away from the skin, when the ostomy collecting bag is worn by a user. In other words, the proximal side is the side closest to the user, when the collecting bag is fitted on a user and the distal side is the opposite side—the side furthest away from the user in use.

The axial direction is defined as the direction of the stoma, when the ostomy collecting bag is worn by a user. Thus, the axial direction is substantially perpendicular to the abdominal surface of the user.

The radial direction is defined as transverse to the axial direction that is transversely to the direction of the stoma.

A collecting bag for use in an ostomy appliance is well-known in the art. In the following, whenever referral is made to a collecting bag, a collecting bag suitable for use in an ostomy appliance is meant. Such a collecting bag may also be referred to as an ostomy collecting bag.

The collecting bag may be made of gas- and liquid impermeable foil-material (for example of polyethylene (PE), polyvinyl-dichloride (PVdC), polyvinyl-chloride (PVC) or ethylene-vinyl-acetate (EVA)), polyurethane (PU) or other polymers that could be used in thermo plastic forming process. For the type of collecting bag that is subject of this invention, the material could be a two-component foil including for example PVdC or a Thermoplastic elastomer or other barrier-layer as the innermost layer and a poly-olefin layer as the outermost. Examples of poly-olefin could be PE, Poly-propylene (PP) or EVA. It is also possible to make a multi layer combination of polymers such as for example a combination of PU, PVdC and EVA to obtain other properties of the extruded polymer. Other examples of materials could be a compounded material made of PE, PP or EVA.

A prior art collecting bag that is welded or glued around the edges, comprises a front wall facing away from the user (on the distal side of the bag) and a rear wall facing the user (on the proximal side of the bag). Likewise, when used, a collecting bag according to this invention comprises a proximal side facing the user and a distal side facing away from the user. The waste inlet opening is provided in the collecting bag in the proximal side and placed in the upper part of the collecting bag so that when a user stands up, the waste inlet opening will be above the midline of the collecting bag. This leaves a larger collecting volume below the waste inlet opening. Thus, the top of the collecting bag is defined as the part closest to the waste inlet opening, and the bottom is defined as the opposite part. The length direction of the collecting bag is defined as the direction from top to bottom of the ostomy collecting bag.

When the collecting bag forms part of an ostomy appliance, the collecting bag may be provided with a waste-inlet opening and the appliance will be provided with attachment means for connecting the collecting bag either directly to the user or to a wafer.

In the extrusion blow-moulding process, the waste inlet opening may be provided by providing the collecting bag with a connector flange during the moulding process and then subsequently cutting this flange off.

In the injection blow-moulding process, the waste inlet opening may already be present in the pre-form.

The attachment means for the collecting bag may be in form of a wafer directly attached to the collecting bag and adapted for directly adhering to the abdominal surface of a user and surrounding the stoma. This provides for a so-called one-piece ostomy appliance.

The attachment means may also be in form of coupling means adapted for releasably coupling to matching coupling means positioned at a wafer which in turn may be adhered to the abdominal surface of a user. This provides for a so-called two-piece ostomy appliance.

The collecting bag according to the first, second and/or third aspect of the invention may be made as a truly three-dimensional collecting bag so that it also has a dimension larger than the combined thickness of the front and the rear of the wall of the bag in the axial direction. In other words, the collecting bag will have a surface area that is larger than the cross-sectional area. A conventional collecting bag will, when empty, only have the dimension corresponding to the sum of the thickness of the front wall and the thickness of the rear wall in the axial direction—and furthermore, the surface area of a conventional collecting bag corresponds to the cross-sectional area.

A three-dimensional collecting bag may provide a larger collecting volume at the lower portion of the collecting bag—towards the bottom of the bag.

The collecting bag according to the invention may have a rounded shape like a balloon. However, the collecting bag may also assume a more elongated shape that is curved or rounded off towards the bottom.

In an embodiment of the invention, the thickness of the wall of the collecting bag is between 50 µm and 200 µm or between 50 µm and 100 µm. The thickness of the wall may be approximately 75 µm. This thickness provides for a good balance between the barrier properties and the flexibility that is needed in the collecting bag for use in an ostomy appliance.

In an embodiment of the invention, the collecting bag is soft and flexible.

By soft and flexible is meant that the collecting bag has a reduced rigidity compared to other types of collecting bags that are not suitable for use in an ostomy appliance.

For example, collecting bags for use in an ostomy appliance may have a tensional modulus of between 50 N/mm$^2$ and 500 N/mm$^2$. The tensional modulus may be measured according to the guidelines given in DIN 53457. Thus in an embodiment of the invention, the wall of the collecting bag has a tensional modulus of between 50 N/mm$^2$ and 500 N/mm$^2$. In a related embodiment, the wall of the collecting bag has a tensional modulus of between 100 N/mm$^2$ and 150 N/mm$^2$. The wall of the collecting bag may have a tensional modulus of approximately 120 N/mm$^2$.

The flexibility of the finished collecting bag depends on the tensional modulus and the thickness of the wall. Thus in an example, the tensional modulus of the wall of the collecting bag is between 100 N/mm$^2$ and 150 N/mm$^2$, e.g. approximately 120 N/mm$^2$ and the thickness of the wall is between 50 µm and 100 µm, e.g. approximately 75 µm. This provides for a soft and flexible collecting bag for use in an ostomy appliance.

In an embodiment, the collecting bag is designed so that it provides a better fit to the body of the user.

For example, the collecting bag may have a curvature in the length direction so that bottom portion is positioned closer to the body, when the bag is worn. This is an advantage if the stoma sits on a top point of a users abdomen e.g. if the user has a bulgy stomach.

One way of doing this is to provide a variation in the rigidity over the wall of the collecting bag so that the front of the wall of the bag (facing away from the user) is more rigid than the rear of the wall of the bag (facing the user). By more rigid is meant that the front of the wall has a tensional modulus that is at least 10% higher than the rear of the wall of the bag. This will have the effect that the rear of the wall of the bag will extend more easily when the bag is filled—and thus the output from the stoma will have a tendency to store itself in the volume of the bag towards the user.

In another embodiment, the collecting bag has a curvature in the length direction so that the bottom portion is positioned away from the body, when the bag is worn. This construction is advantageous if the user has a rather flat abdomen—or if the stoma is sitting in a recess of the users abdomen. In this case the user does not have to carry the output (or the bag) against the surface of the body. This embodiment can be achieved by providing a collecting bag where the rear of the bag is more rigid than the front of the bag.

The variation in rigidity of the wall of the collecting bag can be done by providing a net-structure or a ribbed structure in the surface of the blow-moulding mould. The denseness of the net/ribbed structure will control the rigidity of the wall of the collecting bag so that denser net/ribs will provide a more rigid finished wall-structure. Another way of varying the rigidity of the wall of the ostomy bag is to vary the thickness of the wall of the collecting bag.

In the injection blow-moulding process, this may be done by varying the thickness of the pre-form so that one part of the pre-form is thicker than another part. For example, the part that will become the front of the collecting bag can be thicker than the part that will become the rear of the collecting bag—or vice versa. Furthermore, the variation in rigidity can be done by using a two-component-moulding process in the pre-form so that one part of the pre-form is provided by one type of material and the other is provided of a more rigid type of material.

In the extrusion blow-moulding process, this may be done by varying the thickness of the tube so that one part of the tube is thicker than another part. For example, the part that will become the front of the collecting bag can be thicker than the part that will become the rear of the collecting bag—or vice versa.

In an embodiment, the collecting bag is provided with a ribbed structure obtained by blow-moulding the bag in a mould that is provided with ribs, thereby obtaining a bag that is expandable when filled.

When injection blow-moulding is used, the pre-form may be provided with ribs.

In an embodiment, the ribs may be provided as alternating ribs and grooves extending transversely across the collecting bag. This will provide a bag that is expandable in the length direction. In another embodiment the ribs may be provided as alternating ribs and grooves extending longitudinally along the collecting bag. This will provide a bag that is expandable in the width direction. Typically 15-25 ribs are provided. The depth of the ribs may be between 0.3 mm and 0.7 mm, for example approximately 0.5 mm.

In an embodiment of the invention, at least part of the collecting bag is provided with flex-zones. Providing a collecting bag with flex-zones results in a collecting bag that is more flexible and has improved characteristics for adaptation to the body. Flex-zones can be obtained by providing the blow-moulding mould with a curvature on the inner surface of the mould. Three to four flex-zones extending across the bag are preferable. The flex-zones may have a depth of between 1 mm and 2 mm.

In an embodiment, the pre-form is approximately 3-4 cm long and approximately 1 mm thick. The length is defined as the distance from the attachment means to the end farthest away from the attachment means. A pre-form of this size will be able to be blown up to a finished collecting bag that is approximately 50-200 µm, e.g. 75 µm, thick and having a size suitable for collecting output from a stoma, for example 180 mm×140 mm.

In an embodiment, the pre-form is approximately 1 cm long and has a thickness of 1.5 mm. Such a pre-form will also be able to be blown up in the blow-moulding process to provide a finished collecting bag of for example 180 mm×140 mm. In another embodiment, the pre-form is approximately 15 cm long and has a thickness of about 0.5 mm. Such a pre-form will also be able to be blown up in the blow-moulding process to provide a regular sized finished collecting bag for use in an ostomy appliance of for example 180 mm×140 mm.

In an embodiment, the pre-form may be smaller, for example approximately 1 cm long and approximately 1 mm thick. This provides a small finished collecting bag for use in an ostomy appliance that is generally circular and has a diameter of approximately 100 mm.

In an embodiment, one part of the pre-form has a thickness of approximately 0.75 mm and in another part of the pre-form the thickness is approximately 1.25 mm. This will provide a collecting bag having a part being more rigid than the other. The pre-form may also be provided with several parts of a thickness of e.g. approximately 0.75 mm and several other parts of a thickness of e.g. approximately 1.25 mm. This provides a collecting bag that is more expandable in some parts than in others, i.e. the collecting bag may be more stretchable in some parts than in others.

In an embodiment, the pre-form comprises two different types of material. For example one type of material may be more rigid than another type of material. Different types of material in the pre-form will lead to a finished collecting bag having variation in the material properties, for example variation in flexibility and stretchability. As an example, two different types of PE may be used, one having a tensional modulus of 140 N/mm$^2$ for the front of the wall and another type of PE having a tensional modulus of 100 N/mm$^2$ for the rear of the wall.

The tube (or parison) that is used in the extrusion blow-moulding may be approximately 1 mm thick and have an outer diameter of approximately 30 mm. A tube of this size will be able to be blown up to a finished collecting bag that is approximately 50-200 μm, e.g. 100 μm, thick and (depending on the size of the cavity in the mould) having a size suitable for collecting output from a stoma, for example 180 mm×140 mm. This thickness of the finished collecting bag provides a collecting bag that functions properly in use and is generally soft and flexible and thus suitable for use in an ostomy appliance.

Parts that need to be very precise in the collecting bag may be injection moulded. This includes for example the attachment means. The attachment means, meaning the adhesive base plate, in case of a one-piece ostomy appliance, or the coupling, in case of a two-piece ostomy appliance, may be insert moulded either in the injection moulding process, in case a pre-form is injection moulded, or directly in the blow-moulding process. Insert moulding is done by inserting a finished part into the mould and then injection mould the pre-form or blow-mould the collecting bag at the finished part.

For example, in the blow-moulding process, the attachment means may be positioned in the mould close to the opening into the collecting bag. The cavity of the mould may include a side section to provide room for the attachment means and for leading foil material to the side section. The connection between the attachment means and the collecting bag will occur as a result of the central inner part of the attachment means melting together with the moulded foil material that later constitutes the collecting bag.

In the injection moulding, the connection will occur as a result of the top part of the attachment means melting together with the flange of the pre-form—thus when the pre-form is ready to be put into the blow-moulding mould, it already includes attachment means.

In both processes, the process of welding attachment means to the collecting bag is eliminated.

If the collecting bag is to be provided with a filter, the filter may be insert moulded in the pre-form.

In an embodiment, a cover layer may be inlayed in the blow-moulding mould prior to blow-moulding the collecting bag. In this case the cover layer—e.g. in form of a so-called comfort layer made of non-woven or textile—is already attached to the collecting bag when it exits the blow-moulding process.

EXAMPLES

Extrusion Blow-Moulding Example

A suitable material, e.g. a blend of PE an EVA is extruded in an extruder at 130° C. The extruded blend of PE and EVA is formed as a tube in a ring die and the tube goes into the two part blow mould. The tube could have a thickness of 1 mm, but it could be as low as 0.1 mm and as thick as 4 mm. In this example, the bag is a so called two-piece ostomy appliance. The coupling is, in this case, a part of the bag, and the dimensions and the design of the coupling is integrated in the mould.

When the tube is in the mould, it is blown up to the desired shape. Depending of the design of the mould, the tube will be blown up to a bag, with a preferred thickness between 0.1 and 0.4 mm. The thickness of the finished bag could, however, be as thin as 0.01 mm and as thick as 1.5 mm depending of the choice of extruded polymer and the design of the bag. Also the process in combination with the design of the mould and the temperature distribution in the mould will make it possible to get bags with differentiated thickness of material.

The blowing time is dependent of the thickness and the raw materials, but with a material temperature of 130° C. and an air valve that applies 6 bar pressure, the bag can be blown up to finished shape in less than 1 second. Higher temperature can reduce the time, and the blowing part of the process can be done in less than 0.1 second, if the conditions are right. It is also possible to expand the blowing time to a much longer time, e.g. 10 sec. if needed.

The result is a seamless collecting bag for use in an ostomy appliance with less waste compared to the traditional way of making ostomy collecting bags Injection Blow-Moulding Example First a pre-form is injection moulded. This can be done in a standard injection moulding process. The pre-form could e.g. be made of a blend of PE and EVA or PE, EVA and PVdC or other suitable thermoplastic polymers. The pre-form could be 3 cm long with a diameter of 2 cm and with a thickness 1 mm. The dimensions of the pre-form depend of the materials and the design of the finished bag. The open end of the pre-form could be made with the dimension of a coupling for a two-piece ostomy system. The injection moulding process can make very precise dimensions, hence elements with narrow tolerances can with advantage be finalized in the injection moulded pre-form prior to the blowing process.

After the pre-form has been injection moulded, it is placed in a blow mould form, heated up, and blown into the desired shape and design. An EVA/PE blend could be heated up to 130° C. and then blown up. The blowing time could be approx. 1 sec. but could be as low as 0.1 sec. and as long as 10 sec. if desired. The thickness of the finalized bag will preferable be approx. 0.1 mm, but could also be as low as 0.01 mm and up to 1.5 mm

DETAILED DESCRIPTION OF THE DRAWINGS

Figure 2:
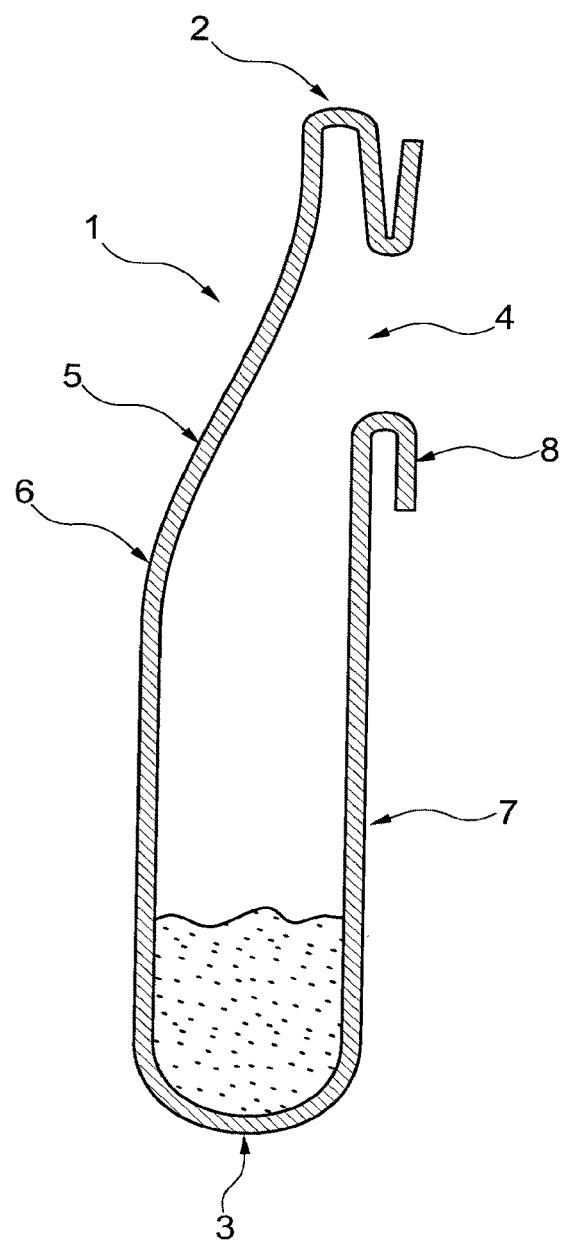
FIGS. 2 to 4 illustrate embodiments of a collecting bag according to the invention.

FIG. 1 illustrates a prior art collecting bag 100 and FIG. 2 illustrates a collecting bag 1 according to the invention. The collecting bag 1 is made by injection moulding a pre-form (see FIG. 5) and then subsequently blow-moulding the finished ostomy bag (see FIG. 6).

A prior art collecting bag 100 as shown in FIG. 1 has a top 101 and a bottom 102 and is made of a front wall 103 and a rear wall 104 of film material and then subsequently sealed (typically welded) along the periphery as indicated at 105. The prior art collecting bag is also provided with a stoma receiving opening 106. Thus, the prior art collecting bag is two-dimensional (flat) prior to use.

FIG. 2 illustrates a collecting bag according to the invention 1. This bag also has a top 2 and a bottom 3 and a stoma receiving opening 4. However, this bag does not comprise any seals—e.g. welds—along the periphery and can therefore be made in a three-dimensional structure as shown in FIG. 2. In other words, the bag is made of one film 5 that may define a front 6 and a rear 7. Thus, when the bag is to be filled, it will already have a three-dimensional structure and the tendency of the sheets to cling to each other will be minimised. Furthermore, problems with the hard and unflexible seal are eliminated.

The flange 8 illustrated in FIG. 2 can be used to attach to attachment means—e.g. by welding or alternatively by insert moulding the attachment means directly to the bag.

Figures 3, 4:
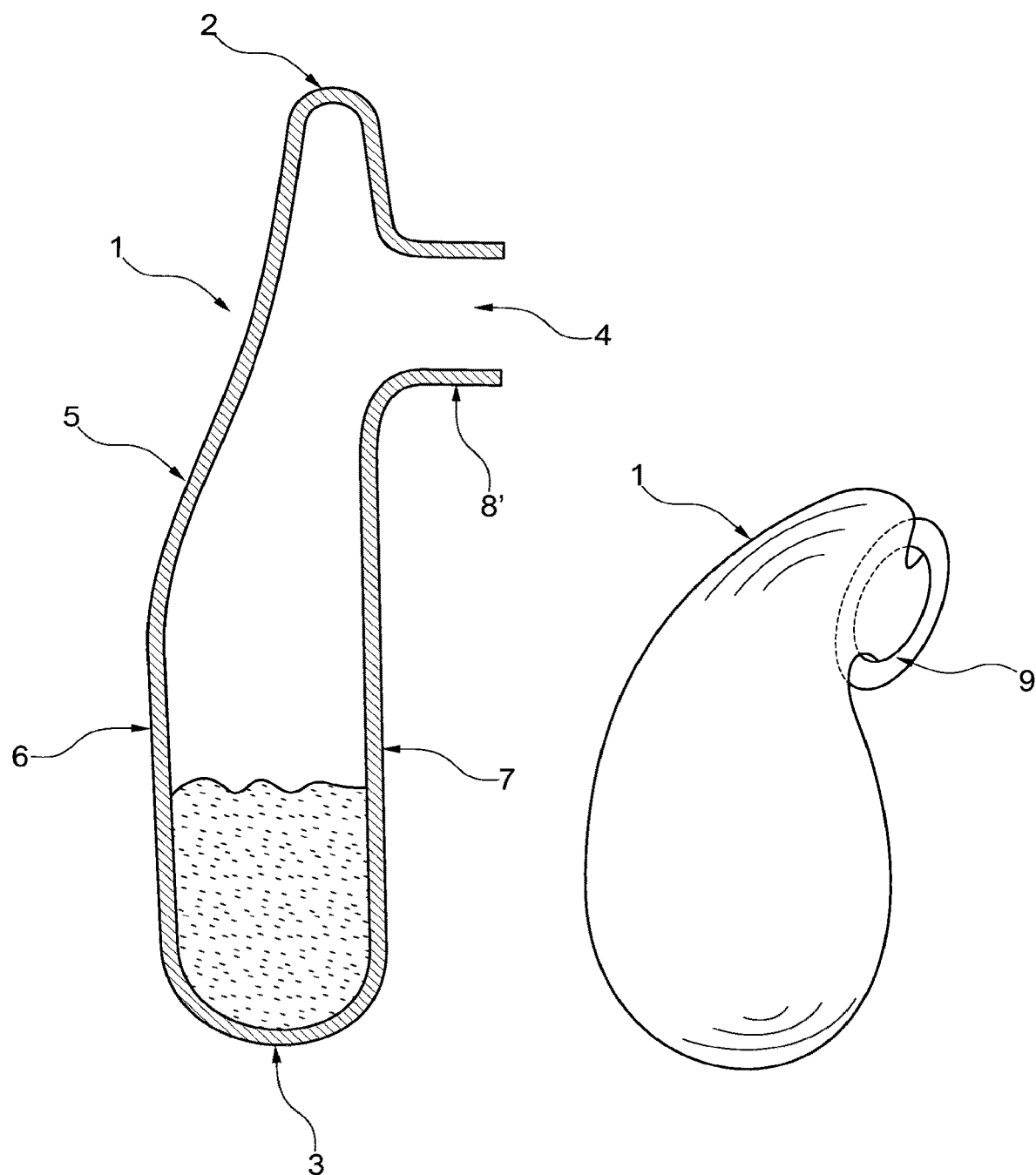

FIG. 3 also illustrates a collecting bag 1 according to the invention. The same reference numbers are used to indicate the same features. This bag is similar to the bag of FIG. 2, the only difference being that the bag of FIG. 3 is obtained by extrusion blow-moulding by extrusion moulding an endless tube (see FIG. 7) and then subsequently blow-mould the finished collecting bag (see FIG. 8).

The collecting bag 1 in FIG. 3 comprises a connector flange 8'. This connector flange 8' can be used to be cut off to define the waste inlet opening into the bag. Then it is possible to later on attach attachment means to the collecting bag—e.g. by welding or adhering. Alternative attachment means can be directly attached to the collecting bag by insert moulding—see FIG. 16.

FIG. 4 illustrates a perspective view of a one-piece ostomy appliance comprising a collecting bag 1 as the one in FIG. 2 or FIG. 3. The ostomy appliance comprises a wafer 9 for adhering the collecting bag to a user. The collecting bag 1 has a rounded shape as indicated in the figure.

Figure 5:
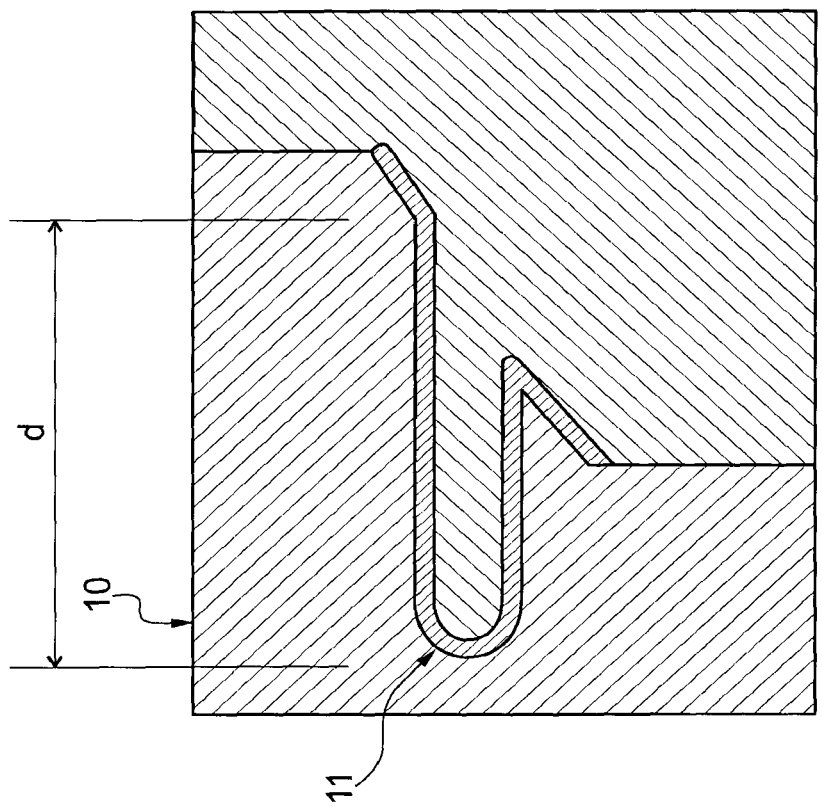
FIG. 5 illustrates a mould for use to injection mould a pre-form.

FIG. 5 illustrates a mould 10 that may be used to mould a pre-form 11 by injection moulding. The pre-form 11 may subsequently be used to form the ostomy collecting bag.

The dimensions of the pre-form may be a tubular element that is approximately 12 mm in outer diameter and 10 mm in inner diameter and 30 mm long, where the length is indicated as d in FIG. 5. This provides a tubular element of approximately 1 mm in cross-section, which when subjected to blow-moulding will be approximately 100 µm thick. The finished ostomy collecting bag will have a size corresponding approximately to a MIDI bag that is 180 mm×140 mm.

Figure 6:
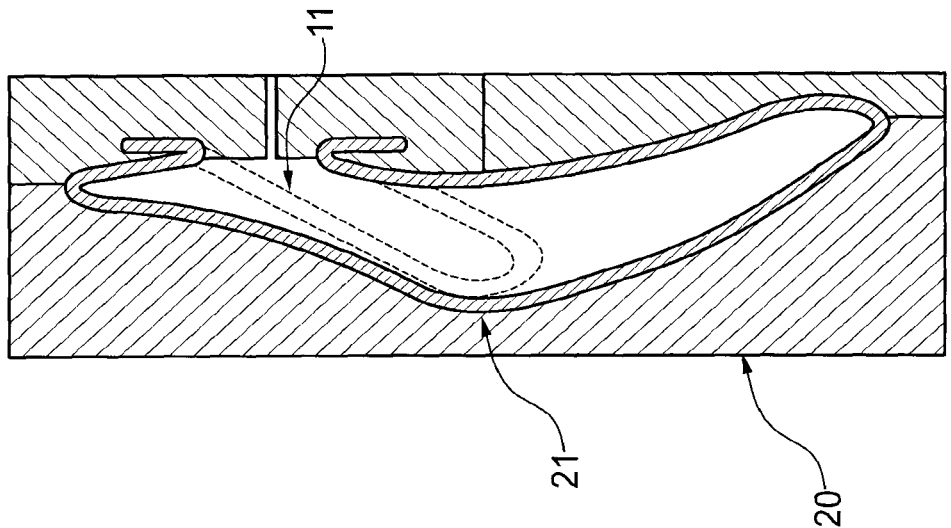
FIG. 6 illustrates a mould for use in a blow-moulding process, the pre-form is indicated in dotted lines.

FIG. 6 illustrates a mould 20 that may be used to mould the finished collecting bag 21. A pre-form 11, obtained by injection moulding, is inserted into the mould 20 and subsequently blown up to provide the finished collecting bag 21.

Figure 7:
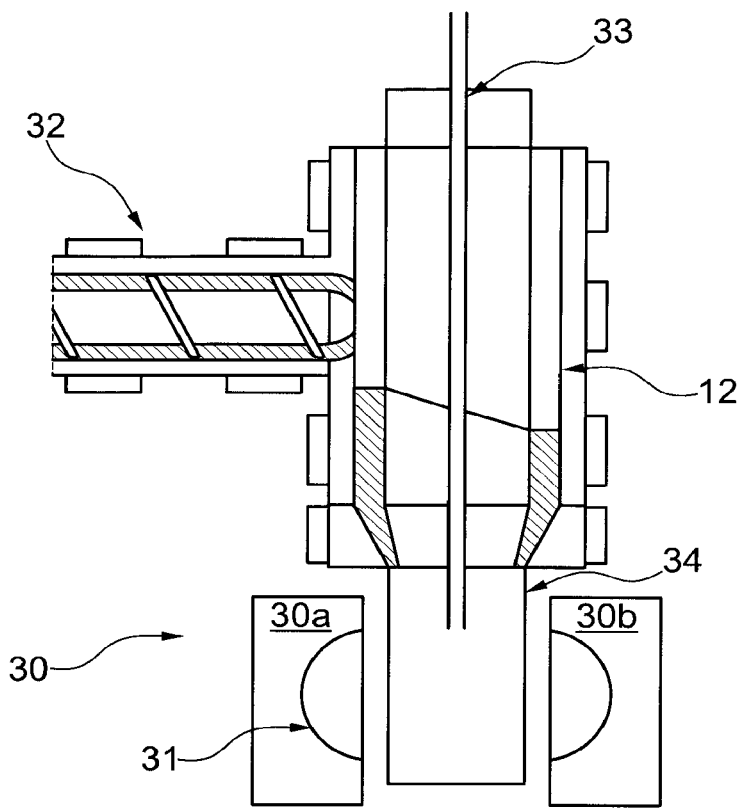
FIG. 7 illustrates a principle sketch of blow-moulding of an endless tube.

FIG. 7 illustrates a principle sketch of parts of a blow-moulding machine that may be used in the invention. The machine comprises a mould 30 with an inner cavity 31. In the sketch the mould consists of two mould halves 30a and 30b. The material is fed into the machine by an extruder 32 that feeds the molten material into a tube or parison 12. The machine also includes a blow-pin 33 to blow the material into contact with the inner surface of the cavity 31. Furthermore, the machine in the sketch includes a plunger or core 34 that keeps the sidewall of the tube 12 to a controlled thickness.

Figure 8:
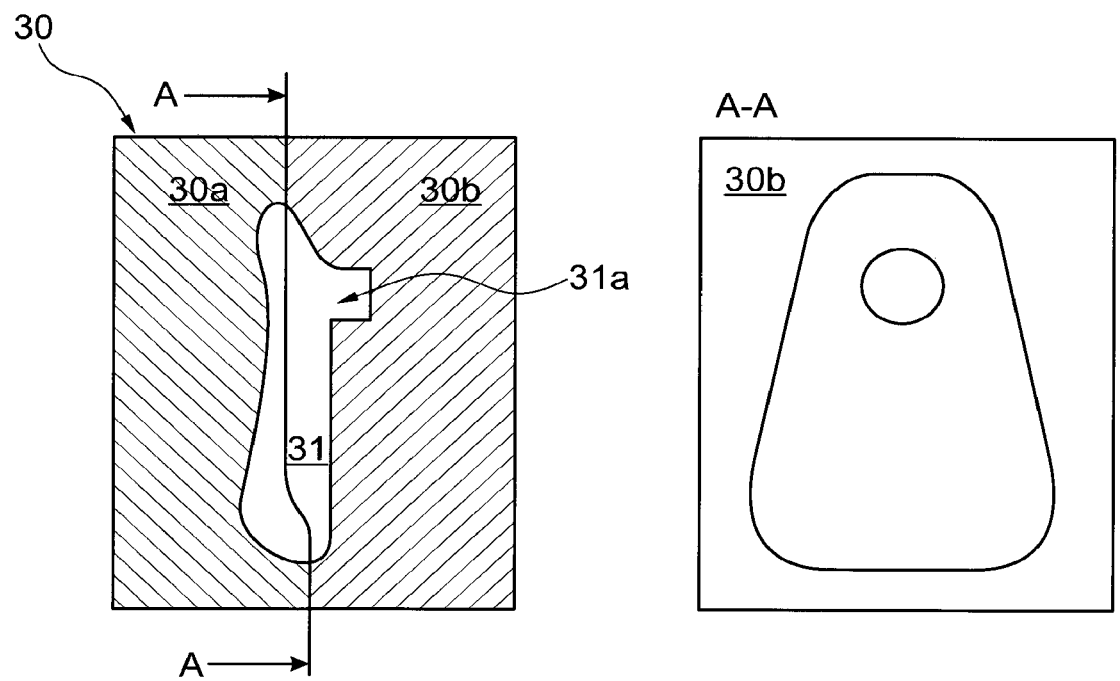
FIG. 8 illustrates the mould for moulding a collecting bag.

FIG. 8 illustrates a collecting bag 1 according to the invention in the closed mould 30. The division between the mould halves 30a and 30b appears from the figure. Furthermore, in the mould, a side section 31a of the inner cavity defines a connector flange 8' for the collecting bag—allowing the finished bag to be provided with a waste inlet opening.

Figure 9:
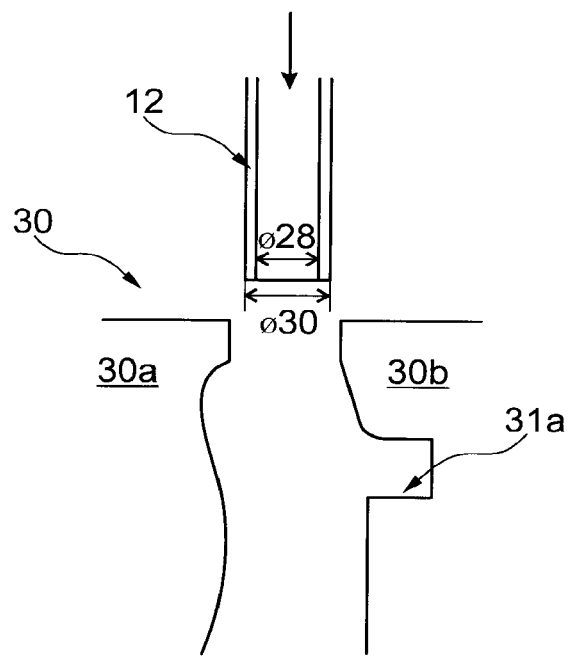
FIG. 9 illustrates insertion of an endless tube into a mould according to the invention.

FIG. 9 illustrates how an endless extruded tube 12 is inserted into the open mould 30. The tube may be approximately 30 mm in outer diameter and may have a thickness of approximately 1 mm in cross-section. When a length of this tube has been subjected to blow-moulding, it will be approximately 100 µm thick. The finished collecting bag will have a size corresponding approximately to a MIDI bag that is 180 mm×140 mm.

Figure 10:
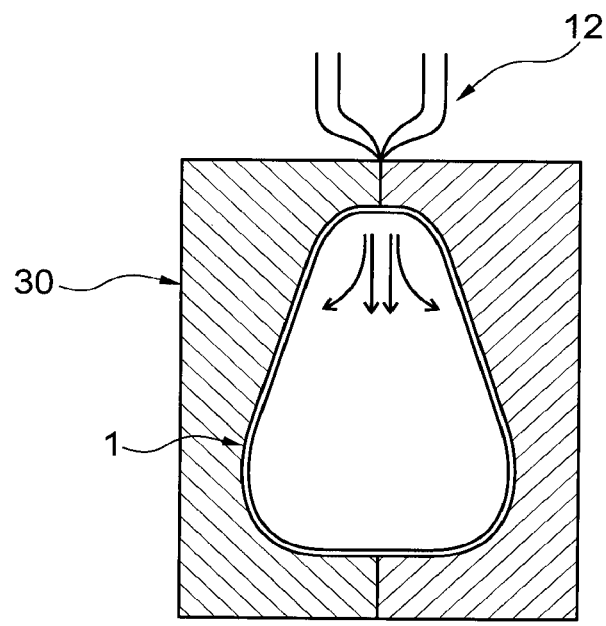
FIG. 10 illustrates how a collecting bag according to the invention is blow-moulded.

FIG. 10 illustrates moulding of the finished collecting bag 1. The length of the tube is blow-moulded inside the mould 30 to provide the finished collecting bag 1. FIG. 10 also illustrates how the next part of the tube 12 is ready to be inserted into the mould 30 to provide the next finished collecting bag.

Figures 11, 12:
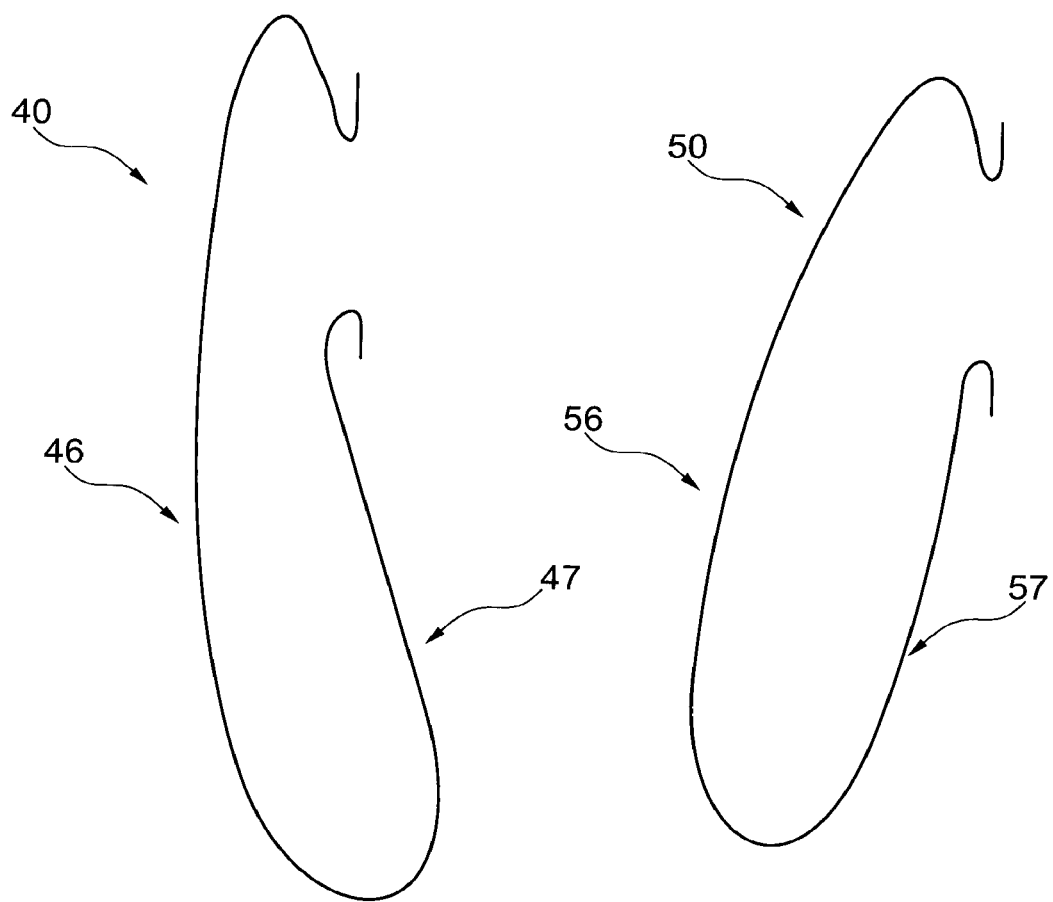
FIGS. 11 and 12 illustrate further embodiments of a collecting bag according to the invention.

FIGS. 11 and 12 illustrate two embodiments 40, 50 of ostomy bags according to the invention. In the ostomy bag 40 illustrated in FIG. 11, the front 46 of the ostomy bag is more rigid than the rear 47 of the bag so that the output will have a tendency to store itself towards the rear 47 of the bag. This has the effect that the output will be stored close to the body and the ostomy bag will not bulge out from the front of the user. In the ostomy bag 50 illustrated in FIG. 12, the front 56 of the ostomy bag is less rigid than the rear 57 of the bag so that the output will have a tendency to store itself towards the front 56 of the bag. This has the effect that the bag will not be in close contact with the body, when it is filled.

Figure 13A:
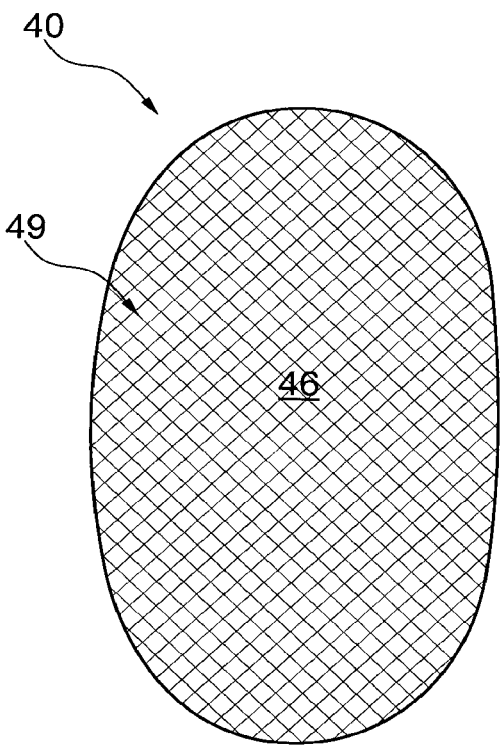
FIGS. 13A and 13B illustrate the collecting bag of FIG. 11 seen from the front and the rear.
Figure 13B:
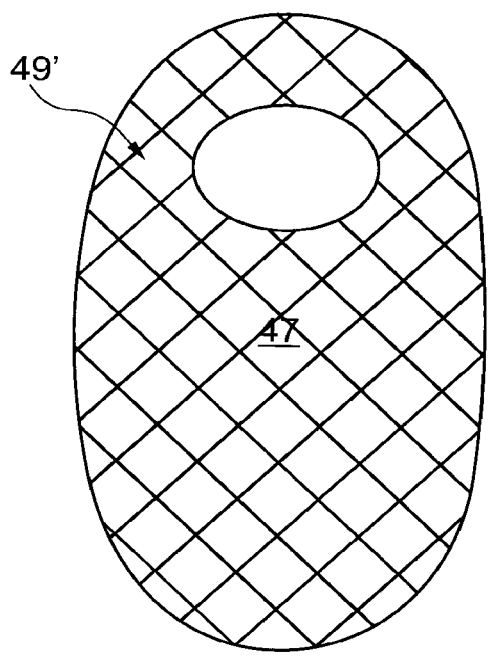

FIGS. 13A and 13B illustrate an ostomy bag 40 as shown in FIG. 11 seen from the front (FIG. 13A) and rear (FIG. 13B) respectively. The front 46 of the bag is more rigid than the rear 47. The difference in rigidity is in this case obtained by providing a net-structure having a dense structure 49 on the front and a more open structure 49' at the rear.

Figure 14A:
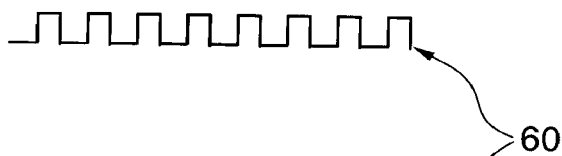
FIGS. 14A and 14B illustrate an expandable cross-section of a collecting bag.
Figure 14B:

FIGS. 14A and 14B illustrate how a ribbed cross-section 60 of an ostomy bag can be used to provide an expandable bag. In FIG. 14A the cross-section 60 is shown in a non-extended configuration and in FIG. 14B the same cross-section is shown when it has been extended.

Figure 15A:
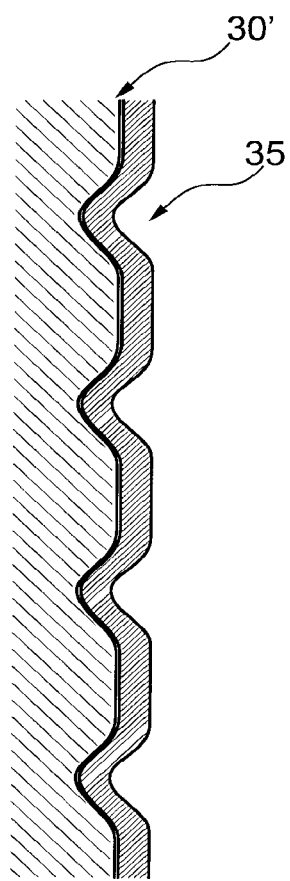
FIGS. 15A and 15B illustrate an extrusion blow-moulded collecting bag with flex-zones.
Figure 15B:
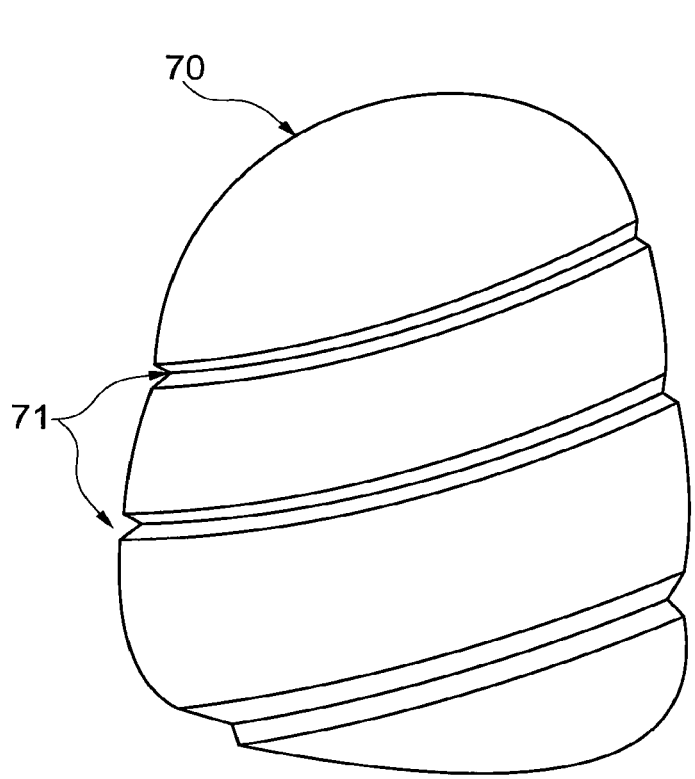

FIGS. 15A and 15B illustrate an extrusion blow-moulded collecting bag 70 with flex zones 71. The flex-zones 71 can be obtained by providing the mould 30' (FIG. 15A) with a curvature 35 corresponding to the flex-zones 71 on the finished bag.

Figure 16:
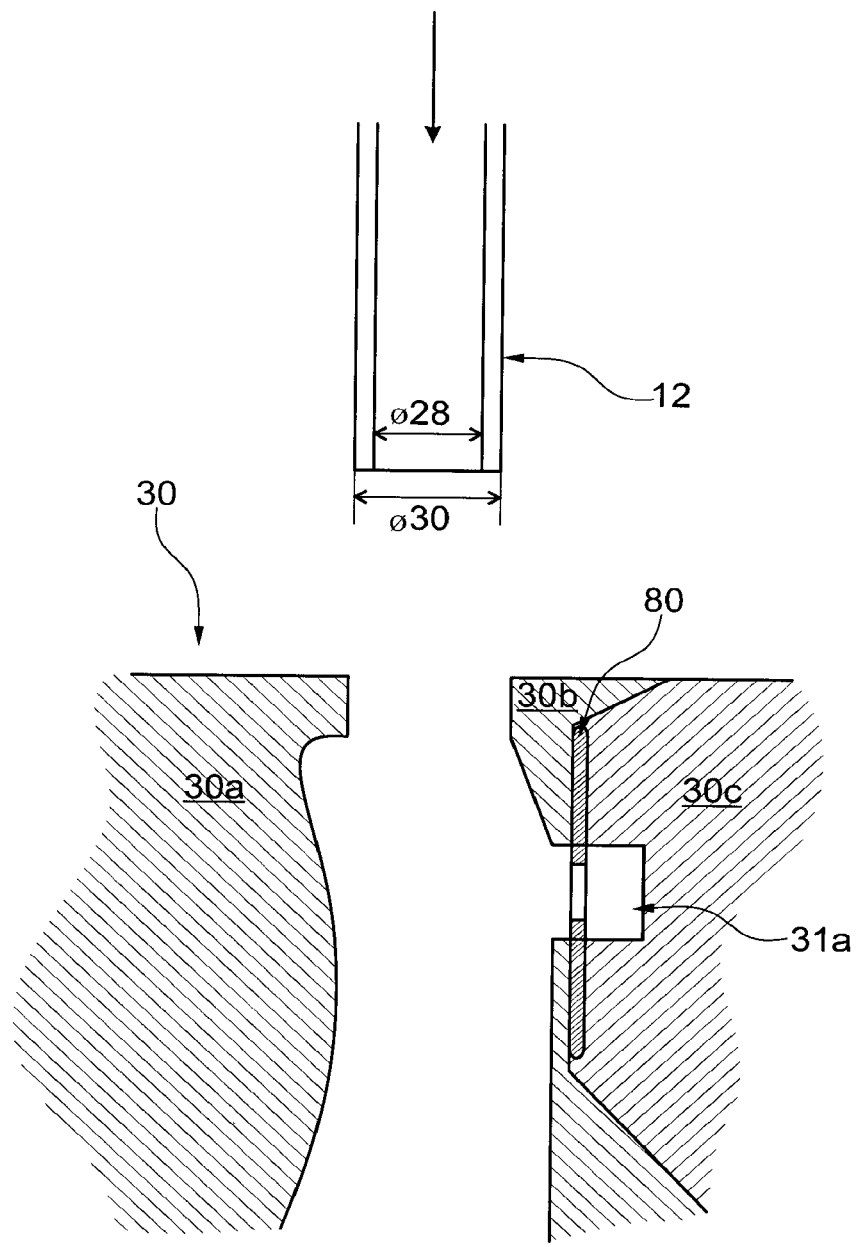
FIG. 16 illustrates how a wafer can be insert moulded to the collecting bag during the blow-moulding process.

FIG. 16 illustrates how attachment means 80 can be insert moulded to the collecting bag during the blow-moulding process. The mould 30 is fed by a tube 12 as described above. To provide the general outline of the collecting bag, the mould comprises two mould halves 30a and 30b to provide the cavity 31 for the collecting bag. The mould 30 is provided with a side section cavity 31a for providing the connector flange that in this case can be used for attaching the attachment means 80 by melting the molten foil material to the attachment means. The attachment means is inserted into the mould between mould half 30b and an additional mould part 30c so that the attachment means 80 are kept in position during the moulding process.

What is claimed is:

1. An ostomy appliance comprising:
    a waste collection bag comprising a single continuous moulded wall and a waste inlet, the moulded wall including a curved bottom, and wherein a transition between the curved bottom and a top of the waste collection bag is smooth and defines a rounded longitudinal curvature; and
    wherein the waste inlet is provided between the top and the curved bottom of the waste collection bag;
    a connector integrally moulded into the waste collection bag around the waste inlet; and
    a filter insert moulded into the waste collection bag above the waste inlet.

2. The ostomy appliance of claim 1, wherein the single continuous moulded wall is formed of a single material having no sealed connection.

3. The ostomy appliance of claim 1, wherein the single continuous moulded wall extends to form a front wall, a side wall, and a rear wall such that the waste collection bag is characterized by an absence of sealed edges.

4. The ostomy appliance of claim 3, wherein the front wall has a tension modulus that is at least 10% greater than a tension modulus of the rear wall to configure the front wall to have a greater rigidity compared to the rear wall.

5. The ostomy appliance of claim 3, wherein the rear wall includes a net structure to provide the rear wall with a greater rigidity compared to the front wall.

6. The ostomy appliance of claim 3, wherein the front wall has a thickness that is greater than a thickness of the rear wall.

7. The ostomy appliance of claim 3, wherein the rear wall has a thickness that is greater than a thickness of the front wall.

8. The ostomy appliance of claim 3, wherein at least one of the front wall and the rear wall is moulded to include a ribbed structure, where the ribbed structure is adapted to allow the waste collection bag to expand when filled.

9. The ostomy appliance of claim 8, wherein at least one of the front wall and the rear wall is moulded to include a net structure.

10. The ostomy appliance of claim 3, wherein at least one of the front wall and the rear wall is moulded to include a transverse patterned structure of alternating ribs and grooves, where the transverse patterned structure is adapted to allow the waste collection bag to expand in a longitudinal direction when filled.

11. The ostomy appliance of claim 3, wherein at least one of the front wall and the rear wall is moulded to include a longitudinal patterned structure of alternating ribs and grooves, where the longitudinal patterned structure is adapted to allow the waste collection bag to expand in a lateral direction when filled.

12. An ostomy appliance comprising:
    a waste collection bag comprising a single continuous moulded wall and a waste inlet, the moulded wall having a curved bottom and, wherein a transition between the curved bottom and a top of the waste collection bag is smooth and defines a rounded longitudinal curvature, and wherein the waste inlet is provided between the curved bottom and the top of the waste collection bag;
    a connector integrally moulded into the waste collection bag around a waste inlet; and
    a filter insert moulded into the waste collection bag;
    wherein the single continuous moulded wall defines a front portion and a rear portion, and at least one of the front portion and the rear portion is moulded to include a patterned structure formed into a surface of one of the front portion and the rear portion to configure the waste collection bag to expand in at least one of a longitudinal direction and a lateral direction when filled.

13. The ostomy appliance of claim 1, further comprising:
    an adhesive base plate integrally moulded into the rear portion of the waste collection bag around the waste inlet and integrated with the connector.

* * * * *